United States Patent
Datt et al.

(10) Patent No.: US 10,293,075 B2
(45) Date of Patent: May 21, 2019

(54) READY-TO-USE, HYDROPHILIC, SELF-DISPERSIVE, FRAGMENTABLE AND BIODEGRADABLE POROUS SPONGE MATRIX AND A METHOD OF MANUFACTURING THEREOF

(71) Applicant: DATT MEDIPRODUCTS LIMITED, New Delhi (IN)

(72) Inventors: Rajan Datt, New Delhi (IN); Ramadhar Kumar, New Delhi (IN); Siddharth Pandey, New Delhi (IN); Pallavi Shrivastava, New Delhi (IN)

(73) Assignee: DATT LIFE SCIENCES PRIVATE LIMITED, New Delhi (IN)

( * ) Notice: Subject to any disclaimer, the term of this patent is extended or adjusted under 35 U.S.C. 154(b) by 130 days.

(21) Appl. No.: 15/081,202

(22) Filed: Mar. 25, 2016

(65) Prior Publication Data
US 2017/0224867 A1    Aug. 10, 2017

(30) Foreign Application Priority Data
Feb. 8, 2016    (IN) .............................. 201611004371

(51) Int. Cl.
*A61F 13/36* (2006.01)
*A61L 24/00* (2006.01)
*A61F 13/20* (2006.01)
*A61L 24/04* (2006.01)

(52) U.S. Cl.
CPC ...... *A61L 24/0036* (2013.01); *A61F 13/2005* (2013.01); *A61F 13/2017* (2013.01); *A61F 13/2074* (2013.01); *A61F 13/2082* (2013.01); *A61F 13/36* (2013.01); *A61L 24/0015* (2013.01); *A61L 24/0042* (2013.01); *A61L 24/043* (2013.01); *A61F 2013/2014* (2013.01); *C08J 2207/10* (2013.01)

(58) Field of Classification Search
None
See application file for complete search history.

(56) References Cited

U.S. PATENT DOCUMENTS

| | | | |
|---|---|---|---|
| 5,836,970 A * | 11/1998 | Pandit | A61L 15/225 602/48 |
| 2014/0276330 A1 * | 9/2014 | Costa | A61F 5/0076 604/8 |

OTHER PUBLICATIONS

Sun et al. (Materials 2013, 6, 1285-1309).*
Dai et al. (J Biomed Biotechnol. 2009;2009:595126).*
IKA (downloaded on Jul. 17, 2017 from URL:< https://www.laboratory-equipment.com/dispersers/T-10-basic-ultra-turrax-disperser-ika.php>).*
Patil et al. (Orient Pharm Exp Med (2011) 11:123-129).*

* cited by examiner

*Primary Examiner* — Sergio Coffa
(74) *Attorney, Agent, or Firm* — Allen, Dyer, Doppelt + Gilchrist, P.A.

(57) ABSTRACT

The invention relates to porous absorbent Composite Material, which may be used e.g. in the form of a plug or tampon, for instance for controlling bleeding, wound closure, prevent tissue adhesion and/or support tissue regeneration. The invention provides a hydrophilic Self-Dispersive, fragmentable and Bio-Absorbable Porous Composite foams, suitable for packing antrum or other cavities of the body, comprising of composite of polymers, which polymer preferably comprises —C(O)—O—; NH2/3+; —OH; —CH2OCH2C(O)O— groups as functional or —CH—O— (e.g. C2H4O; C6H10O5; C6H8O6); —CH—N—O— (e.g. C8H13NO5); O—C—C— (e.g. O—CH2-CH2); —C(O)N— groups in the backbone of the polymers e.g. gelatin, chitosan, collagen, alginate, polyvinyl alcohol, polyethylene glycol, keratin, cellulose.

13 Claims, 1 Drawing Sheet

READY-TO-USE, HYDROPHILIC, SELF-DISPERSIVE, FRAGMENTABLE AND BIODEGRADABLE POROUS SPONGE MATRIX AND A METHOD OF MANUFACTURING THEREOF

CROSS REFERENCE TO RELATED APPLICATION

This application takes priority from and claims the benefit of Indian Patent Application No. 201611004371 filed on Feb. 8, 2016, the contents of which are herein incorporated by reference

BACKGROUND OF THE INVENTION

Field of the Invention

The present invention relates to the field of Medical Biosciences. The present invention provides, generally, porous absorbent materials which are suitable for packing antrum or cavities of the human or animal body.

Particularly, the present invention provides a ready-to-use, self-dispersive, biodegradable and biocompatible device.

More particularly, the invention relates to medical non-woven porous textiles.

Even more particularly, the invention relates to a device to be used as nasal packing in the form of a plug, sheet or tampon, for instance for controlling bleeding, endoscopic sinus surgery, in most common procedures of ear dressing, wound closure, prevent tissue adhesion and/or support tissue regeneration, wound healing process, epistaxis purposes.

The present invention provides a porous scaffold meant as a therapeutic carrier.

The present invention is a sterile product to carry the therapeutic and/or bioactive molecules, biological or chemicals. The present invention provides an art with preference to upregulate and downregulate the process of self-dispersive nature of the porous matrix.

The present invention also relates to a method of preparing such a device for biomedical field.

The terms sponge/matrix/scaffold/device have been used interchangeably throughout the specification and they all refer to the same product, as discussed and covered in the scope of this specification.

Description of the Related Art

Nasal packs are indispensable in ENT practice where the pack is applied to the nasal cavities. The most common purpose of nasal packing is to control bleeding following surgery to the septum or nasal reconstruction, to prevent adhesion or restenosis and to treat epistaxis. Further, the packing is also used to provide support to the septum after surgery.

The range of materials used for this purpose is wide, including both removable and absorbable materials. In cases of septoplasty and rhinoplasty surgery, conventional non-biodegradable packings are frequently removed within 24-48 hours following surgery. In the case of epistaxis, packing is left in for extended periods of time to promote healing and to prevent the patient from touching and accidentally interfering with the recovery of the wound. The packing may be left in the nose for as long as 7-10 days. If the wound is high up in the nasal cavity, packings treated with petrolatum and/or antibiotics are sometimes used. In the art, biodurable wound dressings are used for nasal packing. These biodurable packs have to be removed after several days as described above.

Numerous materials have been proposed in the prior art for use as foams for absorbing or removing body fluids. Conventional packs consisting of gauze or cotton have several disadvantages: the fluid absorption capacity of the material is relatively low, the structure is relatively fragile and individual threads or fibers may break off, erroneous failure to remove the material from the body after internal surgery may lead to serious complications and the material is relatively expensive. Certain hydrophilic synthetic materials intended for biomedical applications have improved properties when compared to conventional materials when it comes to absorption capacities and physico-mechanical properties. Examples of such material are the cross-linked polyurethane-based hydrogels as disclosed in e.g. U.S. Pat. Nos. 3,903,232, 3,961,629, 4,550,126 and EP-A-0 335 669. However, these materials are biodurable and not biodegradable.

The ideal packing would be that which, besides of controlling the hemorrhage and acting as a barrier to adhesion formation, is easily adaptable and reasonably well tolerated by the patient. Numerous packing agents are available, including vaseline-soaked ribbon gauze; fingerstall packs, polyvinyl acetate sponge (Merocel); various balloon tamponade devices. Even if most of them are very effective in what it concerns the hemostasis, these agents cause considerable discomfort for patients, both in terms of pain and bleeding on removal (von Schoenberg M. et. al, Nasal packing after routine nasal surgery—which is not justified. J Laryngol Otol, 1993; 107:902-5; Samad I. et. al, The efficacy of nasal septal surgery. J Otolaryngol, 1992; 21:88-91; Pomerantz J. et. al, Platelet gel for endoscopic sinus surgery. Ann Otol Rhinol Laryngol, 2005; 114:699-704; Vaiman M. et. al, The use of fibrin glue as hemostatic in endonasal operations: a prospective, randomized study. Rhinology, 2002; 40:185-8).

Other complications associated with removable nasal packing (Weber R. et al., Packing in endonasal surgery. Am J Otolaryngol, 2001; 22:306-20; Weber R. et. al, Packing and stents in endonasal surgery. Rhinology, 2000; 38:49-62): septal perforation (due to pressure necrosis); pack dislodgement; aspiration; toxic shock syndrome; foreign body granuloma; myospherulosis; obstructive sleep apnea secondary to nasal obstruction and death.

One of the most important disadvantages of removable nasal packing could be considered its impact on nasal mucosa, and especially on the ciliated mucosal surface area. Animal studies investigating the mucosal trauma caused by removable nasal packing have shown a 50% to 70% loss of the ciliated mucosal surface area in the region of the pack (Shaw C. L. et al., Effect of packing on nasal mucosa of sheep. J Laryngol Otol, 2000; 114:506-9). Therefore, a transient impairment of the patient's innate immune system, the mucociliary clearance, may be associated with the use of removable nasal packing (Chandra R. K. et. al, The effect of FloSeal on mucosal healing after endoscopic sinus surgery: a comparison with thrombinsoaked gelatin foam. Am J Rhinol, 2003; 17:51-5). The impact on patients' quality of life and also the possible complications of removable nasal packing have led to the ongoing development and application of absorbable biomaterials that do not require subsequent removal and still achieve positive effects on hemostasis, promote wound healing, and provide middle turbinate support.

This lack of biodegradability makes such materials less suitable for use in body cavities during surgery, since there is always a possibility that the foam is left accidentally in the body. Furthermore, removing non-biodegradable foams after application in a natural body orifice may be very uncomfortable for a patient and may open up the wound and/or lead to additional scarring of the tissue. In order to prevent these undesired effects, biodegradable sponges or absorbing foams comprising materials of a natural source such as gelatine, proteins, collagen, chitin, chitosan, cellulose or polysaccharides have been suggested.

A wide range of absorbable materials with use in nasal surgery were developed in the last years, including absorbable porcine gelatin (Surgiflo, Ethicon Inc) and thrombin combination; carboxy-methyl-cellulose (CMC, AthroCare); chitosan gel (Department of Chemistry, University of Otago, Dunedin, New Zealand); Fibrin glue (Quixil, Omrix Co.); FloSeal (Baxter International Inc); hyaluronic acid (Mero-Gel, Medtronic); microporous polysaccharide hemispheres (MPH, Medafor Inc); Platelet gel (PPAI Medical); Surgiflo hemostatic matrix combined with thrombin; topical antifibrinolytics such as epsilon-aminocaproic acid (Amicar, Lederle Parenterals Inc) and tranexamic acid (Cyklokapron, Pfizer). NasoPore, Polyganics B. V., Groningen, the Netherlands. However, all of these materials lack the required mechanical strength and have decrete effects on hemostatic, adhesion and healing features. For example, the haemostatic sponge of denaturated gelatin of WO 90/13320 does not have sufficient mechanical strength to stop a severe nose-bleeding, because the compression strength of the material in the wet condition is too low and the sponge liquefies too fast after being applied in the nasal cavity. U.S. Pat. Nos. 3,902,497 and 3,875,937 disclose surgical dressings of bio-absorbable polymers of poly glycolic acid (PGA).

Such materials are, although useful in other applications, not useful in applications where sufficient counter pressure from the foam is required, such as in nose-bleeding, because the material is quite hard and brittle and is not resilient. Moreover, the PGA material is not sufficiently hydrophilic to absorb the blood during severe bleeding. Some hydrophilic synthetic polymers based on polyurethene (WO 2004062704 A1) are used for nasal plug (e.g nasopore, polyganic) but applicability covering all features is not clear. No published literature has investigated the hemostatic or wound-healing properties of polyethylene glycol (NasoPore, Polyganics B. V., Groningen, the Netherlands) after ESS. Further, the mechanical properties are compromised to make it highly fragmentable.

Because of lack of standardization in this matter, still the choice is in the surgeon's hand, according to his abilities, beliefs, or technical possibilities. Now there is generally recognized standard for which types of materials should be used, how longs packs should remain placed, or when placement is indicated. This invention relates current indications, effectiveness and overcoming the risks of nasal packs and stents. The need for absorbable sponges or absorbent foams that can be left in the wound is now well recognized.

Nasal packs should always have smooth surfaces to minimize mucosal damage, improve wound healing and increase patient comfort. Functional endoscopic endonasal sinus surgery allows the use of modern nasal packs, since pressure is no longer required. So called hemostatic/resorbable materials are a first step in this direction. However, they may lead to adhesions and foreign body reactions in mucosal membranes. Simple occlusion is an effective method for creating a moist milieu for improved wound healing and avoiding dryness. Stenting of the frontal sinus is recommended if surgery fails to produce a wide, physiologically shaped drainage path that is sufficiently covered by intact tissue.

Requirements of such foams: a high and rapid absorption capacity, particularly for blood, strength to be readily handled in surgical procedures, conformable so as to fit into any topography, maintenance of tissues' mechanical properties, for a specific period of time during or after surgery or after application of the matrix, soft so as to avoid injury to sensitive tissues. In some instances, the softness of the foam may be increased by wetting of the foam. Therefore, the absorbing foam should also have enough mechanical strength and elasticity in the wet condition and can also be cleared off via natural process to reduce doctors' dependency.

Reference is made to U.S. Pat. No. 9,039,657, titled "Implantable devices and methods for delivering drugs and other substances to treat sinusitis and other disorders" dated 26 May 2015. This invention relates to implantable devices and methods for delivering drugs and other substances to locations within the body of a human or animal subject, to treat or diagnose sinusitis and a variety of other disorders. The invention includes implantable substance delivery devices that comprise reservoirs and barriers that control the rate at which substances pass out of the reservoirs. The delivery devices may be advanced into the body using guide-wires, catheters, ports, introducers and other access apparatus. In some embodiments the delivery devices may be loaded with one or more desired substance before their introduction into the body. In other embodiments the delivery devices are loaded and/or reloaded with a desired substance after the delivery device has been introduced into the body. The present invention relates generally to medical devices and methods and more particularly to substance delivering implants and methods for treating a broad range of disorders including but not limited to sinusitis and other ear, nose and throat disorders.

Further reference is made to United States Patent Application Publication 2004/0116958A1, (now U.S. Pat. No. 8,740,929) titled "Spacing device for releasing active substances in the paranasal sinus" by Gopferich et al, dated 3 Jun. 2014. This invention relates to a tubular sheath or "spacer" formed of biodegradable or non-biodegradable polymer that, prior to insertion in the patient's body, is loaded with a controlled amount of an active substance, such as a corticosteroid or anti-proliferative agent. Surgery is performed to create a fenestration in a frontal sinus and the sheath is inserted into such fenestration. Thereafter, the sheath which has been preloaded with the active substance is inserted into the surgically created fenestration where it a) deters closure of the surgically created fenestration, b) serves as a conduit to facilitate drainage from the sinus and d) delivers the active substance. The sheath of the invention of U.S. Pat. No. 8,740,929 remains substantially in a single configuration (i.e., it does not transition between a collapsed configuration and an expanded configuration) although it may be coated with a material that swells when in contact with mucous or body fluid. In some embodiments, the sheath is formed of multiple layers of polymeric material, one or more of which is/are loaded with the active substance and one or more of which is/are free of the active substance. In other embodiments, the sheath has a "hollow body" which forms a reservoir system wherein the active substance is contained and a membrane which controls the release of the active substance from the reservoir. In some embodiments, the sheath may be anchored by causing the end of the sheath that extends into the sinus to swell or otherwise enlarge.

Another reference is made to U.S. Pat. No. 3,948,254 titled "Novel drug delivery device" by Zaffaroni dated 6 Apr. 1976. This invention relates to implantable drug delivery devices comprising a drug reservoir surrounded by a microporous wall. The reservoir may be formed of a solid drug carrier that is permeable to passage of the drug. The rate of passage of the drug through the wall may be slower than the rate at which the drug passes through the solid drug carrier that forms the reservoir. This invention describes a number of applications for the implantable drug delivery devices including placement in a nasal passage. Specifically, this invention claimed a nasal delivery device for dispensing a drug within a nasal passage at a controlled rate wherein the nasal device is comprised of (a) a wall defining the device dimensioned for insertion and placement within a nasal passage, with the wall formed of a nasal acceptable microporous material, (b) a reservoir surrounded by the wall and comprised of a solid carrier permeable to drug and containing drug in an amount sufficient for the device to meter it at a continuous and controlled rate for a prolonged period of time from the device, (c) a liquid medium permeable to the passage of drug by diffusion charged in the micro-pores, and (d) wherein the device releases drug when in a nasal environment by passage of drug from the carrier and through the liquid to the exterior of the device to produce a useful result. There are also several examples in the patent literature where various sustained release mechanisms have generally been proposed using systems with pre-incorporated drugs into matrices or polymers. These include U.S. Pat. No. 3,948,254 (Zafferoni), US 2003/0185872A2 (now U.S. Pat. No. 7,074,426) (Kochinke), WO 92/15286 (Shikani), and U.S. Pat. No. 5,512,055 (Domb, et al.). In general, these references discuss various materials and structures that may be used to construct sustained drug delivery vehicles and provide a good overview of the state of sustained drug delivery art. These are helpful in laying out certain materials and schemes for creating sustained release systems for drugs.

Further reference is made to U.S. Pat. No. 8,784,893, titled "Polymer formulations for delivery of bioactive agents" dated 22 Jul. 2014. This invention provides compositions comprising a bioresorbable polymer matrix and a bio active agent, wherein the bioactive agent is dispersed within polymer matrix as a solid. Also provided herein are methods for preparing a bioactive agent formulation, wherein the agent is present in a solid form and, wherein the agent is occluded into a polymeric matrix by polymerization of polymer matrix precursors or by self-assembly of the polymer. This invention provides a hydrogel composition formed by combining an aqueous buffer, a thiol-functionalized hyaluronic acid and a crosslinking accelerant in the presence of a gel-persistence-enhancing compound selected from the group consisting of N-acetyl cysteine, glutathione, 2,3-dimercapto-1-propanesulfonic acid, 2,3-dimercapto-1-propanesulfonic acid sodium salt monohydrate, cysteine, dihydrolipoic acid, and pharmaceutically acceptable salts thereof, wherein the hydrogel comprises disulfide cross-links. This composition also comprises an excipient and is having a pH of between 5 and 8 when in aqueous solution. The composition further comprises a bioactive agent as solid particles. The bioactive agent is a steroid, selected from the group consisting of triamcinolone, triamcinolone diacetate, triamcinolone acetonide, triamcinolone hexacetonide, methylprednisolone and dexamethasone. The solid particles have a particle size between about 0.1 micron and 2 mm. The bioactive agent is not covalently bound to the thiol-functionalized hyaluronic acid. The composition forms in about 1 second to 30 minutes after combining the thiol-functionalized hyaluronic acid, the gel-persistence enhancing compound, and the cross-linking accelerant in aqueous buffer. There is also provided a kit for providing a hydrogel composition, the kit comprising container with a thiol-functionalized hyaluronic acid, a gel-persistence enhancing compound, and a cross-linking accelerant and an aqueous buffer. The kit may also comprise another container with a steroid selected from the group consisting of triamcinolone, triamcinolone diacetate, triamcinolone hexacetonide, triamcinolone acetonide, methylprednisolone and dexamethasone.

Another reference is made to U.S. Pat. No. 8,535,709 titled "Agents for controlling biological fluids and methods of use thereof" by Kennedy, et al. 17 Sep. 2013. Therapeutic formulations adapted for positive-pressure application for controlling biological fluid at a desired site in a subject, absorbent articles comprising therapeutic formulations, and anti-infective devices coated with therapeutic formulations, said formulations comprising about 25% to about 99% by weight liquid-crystal forming compound and 0% to about 75% by weight solvent. In addition, methods of using said formulations including methods for controlling biological fluid at a desired site in a subject, methods for controlling blood loss, and methods for facilitating effective closure of a vascular wound or incision site at a desired site in a subject are disclosed, the methods comprising administering particular formulations comprising liquid-crystal forming compounds and solvents that are described herein.

Reference is made to U.S. Pat. No. 8,475,824 titled "Resorbable matrix having elongated particles" by McKay dated 2 Jul. 2013. The invention relates to Compression resistant matrices and methods having elongated particles embedded therein. The compression resistant matrices provide improved stability and mechanical strength and resists shifting, extrusion and rotation after implantation. In some embodiments, the matrices provided reduce or prevent surface compression of the implantable matrix which will cause unwanted increased amounts of growth factor (e.g., bone morphogenic protein) to leak from the matrix.

However, none of the inventions discussed above comprises of featured product and a method to prepare the same as covered in the present invention. The distinguishing features of the present invention as compared to prior art discussed above are very significant and prominent, hence the present invention is novel and inventive over the prior art.

It is a particular objective of the present invention to overcome the drawbacks and the problems associated with the sponges and absorbent foams of the prior art and to provide a biocompatible porous material that is controlled and tunable self-dispersive, biodegradable, that is able to absorb fluids and that has improved and tunable mechanical properties, such as a high elasticity, even when wet.

A self-dispersive, fragmentable and biodegradable porous sponge, made up of lyophilized blend of different polymers synthetic and natural with high flexibility and absorbent capacity, to be used for various biomedical application. The said matrix is prepared using sequential mixing of pre-made solution of polymers and one of them as powdered solid form. The sponge mentioned is soft, highly flexible, porous and hydrophilic in nature. The same is tunable self-dispersive, fragmentable and biosorable at body temperature and pH.

SUMMARY OF THE INVENTION

The main objective of the invention is to provide a porous sponge matrix and a method of manufacturing thereof.

Another objective of the invention is to provide a ready-to-use, hydrophilic, self-dispersive, fragmentable and biodegradable sponge.

A further objective of the invention is to provide a sponge device for porous absorbent materials which are suitable for packing antrum or cavities of the human or animal body.

Another objective of the invention is to provide a method of preparation of such sponge/device.

A further objective of the invention is to provide a porous scaffold meant as therapeutic carrier, more specific as a Hemostasis and packing product.

A further objective of the invention is to provide a device to be used as nasal packing in the form of a plug, sheet or tampon, for instance for controlling bleeding, endoscopic sinus surgery, in most common procedures of ear dressing, wound closure, prevent tissue adhesion and/or support tissue regeneration, wound healing process, epistaxis purposes.

Another objective of the invention is to provide a sterile wound dressing product to carry the therapeutic and/or bioactive molecules, biological or chemicals.

Another objective of the invention is to provide an art with preference to upregulate and downregulate the process of self-dispersiveness and bioaborbability of the porous matrix.

The present invention provides a ready-to-use, hydrophilic, Self-Dispersive, fragmentable and Bio-Absorbable Porous Composite biocompatible device and a method of preparation thereof. The device of present invention comprises a novel porous scaffold composed of polymeric composites and Polyelectrolyte complex (PEC) comprising of composite of polymers. The preferred polymers used comprise functional groups: —C(O)—O—; $NH_{2/3}^+$; —OH; —$CH_2OCH_2C(O)O^-$ groups as functional or —CH—O— (e.g. $C_2H_4O$; $C_6H_{10}O_5$; $C_6H_8O_6$); —CH—N—O— (e.g. $C_8H_{13}NO_5$); O—C—C— (e.g. O—$CH_2$—$CH_2$); —C(O)N— groups in the backbone of the polymers.

The porous matrix is suitable for packing antrum or other cavities of the body and as carrier of plurality of therapeutics to be used as nasal packing in the form of a plug, sheet or tampon, for instance for controlling bleeding, endoscopic sinus surgery, in most common procedures of ear dressing, wound closure, prevent tissue adhesion and/or support tissue regeneration, wound healing process, epistaxis purposes.

Figure 1:
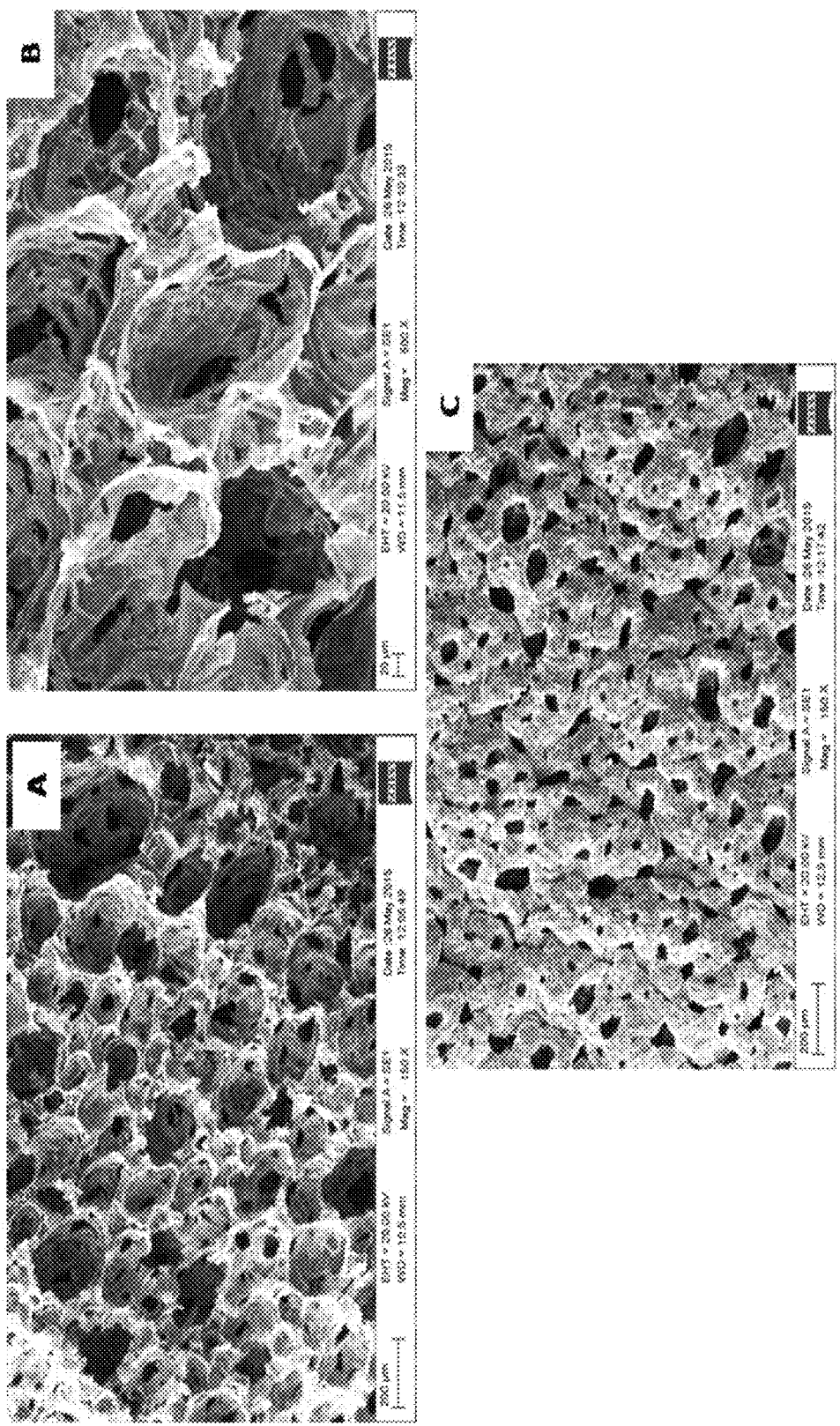
FIG. 1 represents an SEM image of scaffold: A) sectional view; B) sectional view at higher magnification; C) surface view.

Accordingly, the present invention provides a ready-to-use, hydrophilic, self-dispersive, fragmentable and biodegradable porous sponge matrix with high flexibility and absorbent capacity and a method of manufacturing thereof, said sponge is porous having interconnected vesicular micro-voids for holding or encapsulating the therapeutics/drugs/cells inside, with large surface area and micro-areas for reactions to occur, said sponge is obtained using lyophilized blend of polymers, preferably sequential mixing of two or more polymers followed by homogenization with specific aspect ratio of shaft, impeller and vessel of the system for mixing, for a definite period of time, such that the resulting matrix sponge performs at significant level for using in various biomedical applications.

DETAILED OF THE SEVERAL EMBODIMENTS

It should be noted that the particular description and embodiments set forth in the specification below are merely exemplary of the wide variety and arrangement of instructions which can be employed with the present invention. The present invention may be embodied in other specific forms without departing from the spirit or essential characteristics thereof. All the features disclosed in this specification may be replaced by similar other or alternative features performing similar or same or equivalent purposes. Thus, unless expressly stated otherwise, they all are within the scope of present invention. Various modifications or substitutions are also possible without departing from the scope or spirit of the present invention. Therefore, it is to be understood that this specification has been described by way of the most preferred embodiments and for the purposes of illustration and not limitation.

The present invention provides a generally, porous absorbent materials which are suitable for packing antrum or cavities of the human or animal body and method of preparation thereof. The device of present invention is a novel porous scaffold to be used as nasal packing in the form of a plug, sheet or tampon, for instance for controlling bleeding, endoscopic sinus surgery, in most common procedures of ear dressing, wound closure, prevent tissue adhesion and/or support tissue regeneration, wound healing process, epistaxis purposes.

The present invention basically relates to the efficient deployment of a biodegradable, biocompatible medical aid through a novel highly porous scaffold that can be deployed at the point of proposed use. The scaffold under the present invention allows the medical aid suitable for packing antrum or cavities of the human or animal body with an ability to stop bleeding and also reduce dependency on medical staff, preserve tissue after injury and facilitate surgical speed.

The present invention is a hydrophilic self-dispersive, fragmentable and bio-absorbable porous composite foam/sponge, suitable for packing antrum or other cavities of the body. The sponge preferably comprises polymers having functional groups —C(O)—O—; $NH_{2/3}^+$; —OH; —$CH_2OCH_2C(O)O^-$ groups as functional or —CH—O— (e.g. $C_2H_4O$; $C_6H_{10}O_5$; $C_6H_8O_6$); —CH—N—O— (e.g. $C_8H_{13}NO_5$); O—C—C— (e.g. O—$CH_2$—$CH_2$); —C(O)N— groups in the backbone of the polymers.

The said spongy patch under the present invention consists of synthetic and natural polymers to name a few polyvinylalcohol, alginic acid salt, modified cellulose, gelatin, chitosan and other having the groups mentioned before. The said sponge can be impregnated with therapeutics such as growth factors, antioxidants, clotting agents for instance, including but not limited to thrombin, calcium chloride ($CaCl_2$), polyphenol, and tranexamic acid. The same can also be impregnated with biological materials such as cells e.g. primary cells and stem cells. These constituents are held in the vesicular voids of the matrix, on the internal surface of the sponge which are able to act rapidly when blood flows into the dressing. Once the scaffold under the present invention is in contact with blood, the dressing enables sealing and stabilization of wound surfaces.

The said sponge/foam is a porous scaffold characterized in that the structure is reticulate and has an inner surface considerably larger than its outer surface, that it contains hollow spaces, pores within the reticulate structure and that it can absorb many times its own weight in liquids in a short period of time. On the other hand, it may be used for wound closure, e.g. to prevent infection and/or tissue adhesion, or for tissue regeneration purpose (cell in-growth into pores).

Such sponge/foams are the subject of the present invention and are also referred to as absorbent foams/sponges. The said sponge/foam are biodegradable as the ability of a polymer to be acted upon biochemically in general by living cells or organisms or part of these systems, including hydrolysis, and to degrade and disintegrate into chemical or biochemical products. Further, the invention is bioresorbable feature, i.e. it comprises an ability of being completely metabolized by the human or animal body making this packing suitable for internal body application.

The novel scaffold under the present invention provides a highly soft, smooth and exudates absorbency property to the scaffold. The presence of hydrophilic group in the matrix of the polymer from which the foam of the invention is comprised further provides said foam with required characteristics such as the capacity to absorb aqueous liquids and being readily biodegradable, bioresorbable and self-dispersive to get naturally clean off from the cavity/antrum such as nasal sinuses.

The polymer of the present invention may be produced in bulk, or, more preferably, it may be produced in a solvent. A very suitable such solvent is water or acidified water. The advantage of producing a polymer of the present invention in said solvent is that a very advantageous starting material is thus provided for the preparation of sponge of the invention. This starting material is already present in the form of a solution, and no time consuming dissolution of polymers in solvents needs to be accomplished. Most preferred is the use of the solvent acidified water. The one of the polymers used must be added as solid powdered form.

The present invention aims to overcome the problems in the existing prior arts and provides the novel and unique features in the scaffold by providing on-demand services for nasal packing sponge with high porosity and regulated pores on the same platform of a matrix. The technologies involved are the timed patterned physico-chemical treatment of the two or more polymers used stated above using a very simplified process to obtain tunable self-dispersive interaction and orientation between the molecules out of all at least one of the preferred polymers, which are used in form of powder solid. The used technology provides the proper interaction and orientation between the functional and backbone groups of the polymers used, resulted into a typical polyelectrolyte complex (PEC) and polymer sandwich.

The present invention provides the requirements of such sponge with a high and rapid absorption capacity, particularly for blood, strength to be readily handled in surgical procedures, conformable so as to fit into any topography, maintenance of tissues' mechanical properties, for a specific period of time during or after surgery or after application of the matrix, soft so as to avoid injury to sensitive tissues. In some instances, the softness of the foam may be increased by wetting of the foam. Therefore, the absorbing foam should also have enough mechanical strength and elasticity in the wet condition and can also be cleared off via natural process to reduce doctors' dependency.

Further, the present invention is to overcome the drawbacks and the problems associated with the sponges and absorbent foams of the prior art and to provide a biocompatible porous material that is controlled and tunable self-dispersive, biodegradable, that is able to absorb fluids and that has improved and tunable mechanical properties, such as a high elasticity, even when wet.

A ready-to-use, hydrophilic, self-dispersive, fragmentable and biodegradable porous sponge with high flexibility and absorbent capacity, made up of lyophilized blend of different polymers, to be used for various biomedical application. The said matrix is prepared using sequential mixing of pre-made solution of polymers and one of them as powdered solid form. The sponge mentioned is soft, highly flexible, porous and hydrophilic in nature. The resulting product is tunable self-dispersive, fragmentable and biosorable at body temperature and pH. Further, the interconnected vesicular micro-voids hold the drug/cells inside and as a result the encapsulated therapeutics of the matrix perform at significant level. Further the highly porous structure of the present invention results into interconnected small voids, provide a large surface area and micro-areas for reactions to occur and thus exert a pseudo-catalytic effect on blood clotting. The PEC containing micro-mesh and body's fibrinogen converted into fibrin forms an efficacious plug and prevents the loss of blood and stops the loss of clotting factor. The novel device of the present invention makes the product light weighted, to be more physical and also altering the blood clotting mechanism. The scaffold of the present invention can be removed easily usually without causing additional/secondary hemorrhage from the application site.

The novel porous scaffold of the present invention is also capable of being used as a carrier for other therapeutics/bioactive molecules/cell (primary or stem cell) towards tissue engineering and other biomaterial applications. Moreover, the scaffold of the present invention is also capable of being used as a cover for the compromised tissues either as acellular or cellular product.

The utilization of more than one type of polymer & their properties for multi-therapeutics loaded preparation and impregnation of the same with PEC scaffold, a system for more than one types of the pharmaceuticals (like clotting factors, co-factors, clot stabilizers, antibiotics, analgesics, anti-allergic, antioxidants, growth factors, etc.) to get delivered in phase-wise and controlled manner for extended period of time.

The novel aspect of the present invention is the sequential timed patterned physico-chemical treatment of the synthetic and natural polymers by using a very simplified process to obtain a highly flexible stabilized tunable self-dispersive porous scaffold, which can be further tuned using any cross-linker, if required. Further, the invention comprises the preparation of said PEC containing sponge, which is achieved using a specific aspect ratio of shaft, impeller and vessel of the system for mixing. One of the ingredient polymers is added in powder form and rest are in solution from using the water or acidified water as solvent.

The present invention comprises polyelectrolyte complex such as of gelatin and alginate in porous sponge. The present invention provides, a method for preparing a biodegradable absorbent sponge/foam suitable for as hemostatic sponge, wound dressing material, packing antrum or other cavities of the human or animal body, including dental packs, or as a drug delivery vehicle, comprises preparing a polymer according to the invention in acidified water or water, diluting the polymer solution during interaction of the functional and backbone group of the polymers with the solvent and the polymer solution, freezing the reaction mixture, and subliming the solvent, under vacuum at low temperature.

The invention also provides a process for preparing said sponge scaffold, which is provided below in detail:

In a preferred embodiment, said polymers are preferably selected from but not limited to gelatin, chitosan, collagen, alginate, polyethylene glycol, polyvinyl Pyrrolidone, polyvinyl alcohol, polyurethane, keratin, Carboxy-methyl cellulose, gelatin hydrolysate, chitosan hydrolysate, partially denatured collagen and/or synthetic or naturally derived molecules such as phytochemicals.

In another embodiment, said therapeutics and pharmaceuticals are selected from but not limited to Tannic acid, Catechin family, tranexamic acid, calcium chloride, thrombin and/or glucosamine, Polylysine.

In a preferred embodiment, said sponge/scaffold is produced by the steps:
a) preparing a homogeneous solution of the individual polymers with different ratio in water or in water and acetic acid and subjecting for hot air treatment to obtain polymer solution at 50-90 degree C.;
b) mixing of polymer solution obtained in step (a) at controlled parameters (18°-25° C. and 55±5% RH) and sequential manner to obtain polymer composite solution (illustrated in Example 1);
c) mixing of powder form solid of one of polymers to obtain final polymer composite solution obtained in step (b) containing PEC followed by freezing and drying at low temperature under vacuum, respectively at −80° C. and −5° C. for 4000 min;
d) Cutting the above obtained porous scaffold/sponge/foam obtained at the end of step (c) as per requirement at 18°-25° C. and 55±5% RH.
e) Optionally, the obtained scaffolds in steps (c) & (d) are subjected for the stabilization either by ammonia vapor or ammonia solution or alkali solution following aldehyde vapor or EDC as per requirement for 10-12 hrs at 18°-25° C. and 55±5% RH.
f) subsequently treatment of the obtained scaffold in step (d) & (e) under vacuum at 25-40 degree C. overnight (10-12 hrs);
g) Followed by gamma irradiation of the scaffold obtained in steps (d) & (f) to obtain the final ready to use product.
h) Optionally, loading the required pharmaceutical/therapeutic solution containing different ratio of drugs as per the requirement into the obtained scaffold in step (f) followed by step (g) to obtain the final ready to use product at 18°-25° C. and 55±5% RH.
i) Optionally, loading the required cells (primary/stem cells) as per the requirement into the obtained scaffold in step (g) under aseptic condition to obtain the final ready to use product at 18°-25° C. and 55±5% RH.

In another embodiment, said method involves physico-chemical treatment of said polymers using a very simplified process in order to obtain a stable molecular interaction and orientation between the molecules of the said polymers, causing an interaction and orientation between the functional groups of the polymers used, resulting into a typical polyelectrolyte complex (PEC), so as to obtain a highly porous matrix.

Accordingly, the present invention provides a ready-to-use, hydrophilic, self-dispersive, fragmentable and biodegradable porous sponge matrix and a method of manufacturing thereof, said sponge is porous having interconnected vesicular micro-voids for holding or encapsulating the therapeutics/drugs/cells inside, with large surface area and microareas for reactions to occur, said sponge is obtained using lyophilized blend and sequential mixing of two or more biopolymers with high flexibility and absorbent capacity, followed by homogenization with specific aspect ratio of shaft, impeller and vessel of the system for mixing, for a definite period of time, such that the resulting matrix sponge performs at significant level for using in various biomedical applications.

In an embodiment, said sponge is prepared using sequential mixing of pre-made solution of polymers with one of them as powdered solid form to get differential solubility of polymer complex and tunable self-dispersiveness, fragmentability and bioabsorbility and thus obtained homogenized composite mixture is casted immediately within a time limit.

In another embodiment, said sponge is soft, highly flexible, porous, hydrophilic, self-dispersive, fragmentable in nature and is biosorable at body temperature and pH.

In another embodiment, said polymers used for synthesizing said sponge are preferably selected from but not limited to gelatin, chitosan, collagen, alginate, polyvinyl alcohol, poly(vinyl pyyrolidone), polyurethane, polyethylene glycol, polypropylene glycol keratin, hyaluronic acid, carboxymethyl cellulose, gelatin hydrolysate, chitosan hydrolysate, partially denatured collagen and/or synthetic or naturally derived molecules such as mucilaginous polysaccharides.

In yet another embodiment, said sponge is obtained by mixing different polymer solutions preferably polyvinyl chloride (5%-15%), Gelatin (2%-7%), Sodium Alginate (0.5%-2%) polyethylene glycol-200 (1 ml-5 ml), and chitosan (0.5%-1%).

In another embodiment, the sequential timed patterned physico-chemical treatment of polymers is preferably dissolution of polymers to form the solution with concentration mentioned in claim 5 at temperature 40-70° C. preferably
  Stirring of the polymer blend temp 18-25° C., 55±5% RH for 20-30 min using a stirrer with aspect ratio of the diameter of container and impeller ranging between 1.17 to 1.57 for 20 mins at the 1000-3600 rpm.
  Adding of acid preferably glacial acetic acid (0.5-2.5%) at rate of 1 ml/min and at temp 18-25° C., 55±5% RH for 5-10 min.
  adding of solid powder preferably of chitosan, 0.5%-1.2% final concentration at the rate of 1 mg/ml at temp 18-25° C., 55±5% RH for 30-40 min.

In another embodiment, said mucilaginous polysaccharides are obtained from various plants sources like Irish moss, Marshmallow roots, Fenugreek seed, Flax seeds, *Psyllium* husk seed and any other equivalent.

In another embodiment, said mucilaginous plant extract mentioned is obtained using a sequential method of dilution, filtration and by drying the plant source and then dissolving in ultrapure water to prepare a solution of concentration 0.2%-1% followed by thermal treatment; diluting the solution thus obtained 2-3 times and homogenizing to form a homogenized solution for 23-30 min at 18-25° C., 55±5% RH; filtering the homogenized solution and subjecting to 55° C. under hot air for 12-15 hr; using the dried extract ranging from 0.5% to 2% to obtain the desired sponge.

In another embodiment, said sponge is prepared in the same manner using the mucilaginous polysaccharide extract solution of concentration ranging from 0.4% to 1.5%.

In yet another embodiment, said sponge is stabilized and tuned using different chemicals and radiation or a combination of both, wherein said chemicals are preferably selected from but not limited to glutaraldehyde, formaldehyde, EDC, ammonia, and using solution or vapor to form a stable cross linked matrix following treatment with ammonia vapor and preferably followed by Gamma irradiation.

In another embodiment, said sponge can degrade thermally and can be easily removed from the site of application in the body cavity. In another embodiment, said sponge comprises interconnected small voids, providing a large surface area and micro-areas which is hydrophilic in nature and retains water, resulting in formation of soft flexible dressing which provides support for the healing tissue in nasal cavity and external auditory meatus.

In another embodiment, said sponge is used for various applications like dressing for nasal interventions, ear and other body cavities, absorbent foam dressing for exudating wounds, diabetic foot ulcers, venous ulcers, as a drug and cell carrier and cell growth matrix, as carrier for various therapeutic and antimicrobial agents, nanoparticles, etc., as a cover for the compromised tissues, as a dressing for body cavity where it is difficult to cover the wound using traditional dressing methods.

In an embodiment, said sponge is preferably prepared in the form of a plug, tampon or sheet.

Advantages of the Invention

Product has a high and rapid absorption capacity for fluids, particularly for blood
Good strength to be readily handled in surgical procedures
Conformable so as to fit into any topography
Good mechanical strength and elasticity in the wet condition
Easy to clear-off via natural process to reduce doctors' dependency
Light weight in nature
Easy to remove without causing additional/secondary hemorrhage from the application site

EXAMPLES

The following example is for the purposes of illustration only and therefore should not be construed to limit the scope of the present invention:

Example 1

Take 30 ml of 7.5% PVA solution at 3300 RPM, 22 degree C. and add 15 ml of 10% Gelatin solution to it to get mixture B. Add 15 ml of 1% Alginate solution to mixture B to get mixture C at 2800 RPM, 22 degree C. Add 3 ml of PEG-200 to mixture C to get mixture D at 3000 RPM, 22 degree C. Following this add 30 ml of mucilage (1%) to the solution mixture D stir using homogenizer for 20 min at 2300 RPM, 22 degree C. and then add 0.75 ml of Acetic acid and homogenize for 1 min to get mixture E. Add 0.75 gm of chitosan to mixture E and homogenize for 30 min at 1800 RPM, 22 degree C. Cast the samples in Teflon tray followed by drying at low temperature under vacuum. Cut the sample into the desirable size and shape followed by stabilization and gamma irradiation.

What is claimed is:
1. A method of manufacturing a biodegradable porous sponge matrix, comprising the steps of:
preparing a homogenous solution of at least two polymers by adding a first polymer to water to form a first polymer solution, and adding a second polymer to the first polymer solution to form a homogenous solution of the at least two polymers;
wherein the step of preparing the homogenous solution of the at least two polymers further comprises dissolving of the at least two polymers to form the homogenous solution, wherein the step of dissolving comprises stirring of the at least two polymers at a temperature between 18-25° C., and at a relative humidity of 50-60% for between 20-30 minutes using a stirrer with an aspect ratio of the diameter of the container between 1.17 to 1.57 and between a rate of 1000-3600 rpm;
introducing glacial acetic acid at a concentration between 0.5-2.5% w/v at rate of about 1 ml/minute and at a temperature between 18-25° C., and a relative humidity between 50-60% for between 5-10 minutes;
introducing chitosan at a concentration between 0.5% to 1.2% w/v at the rate of about 1 mg/ml and at a temperature between 18-25° C., and a relative humidity between 50-60% for between 30-40 minutes;
allowing the homogenous solution to freeze dry, thereby obtaining a porous sponge matrix; and
wherein each polymer is selected from the group consisting of: gelatin, chitosan, collagen, alginate, polyvinyl alcohol, poly(vinyl pyrrolidone), polyurethane, polyethylene glycol, polypropylene glycol keratin, hyaluronic acid, carboxymethyl cellulose, gelatin hydrolysate, chitosan hydrolysate, partially denatured collagen and mucilaginous polysaccharides.

2. The method of manufacturing the biodegradable porous sponge matrix of claim 1, further comprising:
mixing different polymer solutions selected from the group consisting of: polyvinyl chloride (5%-15% w/v), Gelatin (2%-7% w/v), Sodium Alginate (0.5%-2% w/v) ~polyethylene glycol-200 (1%-5% v/v), chitosan (0.5%-1% w/v).

3. The method of manufacturing the biodegradable porous sponge matrix of claim 1, wherein said mucilaginous polysaccharides are obtained from sources selected from the group consisting of: Irish moss, Marshmallow roots, Fenugreek seed, Flax seeds, and *Psyllium* husk seed.

4. The method of manufacturing the biodegradable porous sponge matrix of claim 3, wherein said mucilaginous polysaccharides comprise a mucilaginous plant extract that is obtained by:
utilizing a sequential method of dilution, filtration and drying of a selected plant source comprising:
preparing a solution of the plant extract by dissolving the plant extract in water at a concentration 0.2%-1% w/v followed by thermal treatment of the solution;
diluting the solution obtained 2-3 additional times;
exposing the solution to a temperature between 18-25° C., and a relative humidity between 50-60% for 23-30 min to create a homogenous solution;
filtering the homogenized solution and subjecting the homogenized solution to a temperature of 55° C. under heat for 12-15 hours to create a dried extract; and
utilizing the dried extract at a concentration of 0.5% to 2% w/v to obtain prepare the porous sponge.

5. The method of manufacturing the biodegradable porous sponge matrix of claim 1, further comprising:
stabilizing the sponge utilizing at least one chemical selected from the group consisting of: glutaraldehyde, formaldehyde, 1-Ethyl-3-(3-dimethylaminopropyl) carbodiimide, and ammonia; and
exposing the sponge to gamma irradiation.

6. The method of manufacturing the biodegradable porous sponge matrix of claim 1, wherein said sponge has ability to degrade thermally and is easily removed from the site of application in the body cavity.

7. The method of manufacturing the biodegradable porous sponge matrix of claim 1, wherein said sponge is used for applications selected from the group consisting of: a dressing for nasal interventions, body cavities, an absorbent foam dressing for exudating wounds, a diabetic foot ulcers, venous ulcers, as a drug and cell carrier and cell growth matrix, as a carrier for various therapeutic and antimicrobial agents, nanoparticles, as a cover for the compromised tissues, and a dressing for body cavity where it is difficult to cover the wound using traditional dressing methods.

8. The method of manufacturing the biodegradable porous sponge matrix of claim 1, wherein said sponge is preferably prepared in the form selected from the group consisting of: a plug, tampon and sheet.

9. The method of manufacturing the biodegradable porous sponge matrix of claim 1, wherein said sponge is soft, flexible, porous, hydrophilic, self-dispersive, fragmentable in nature and is biosorable at body temperature and pH.

10. The method of manufacturing the biodegradable porous sponge matrix of claim 1, wherein said sponge comprises interconnected vesicular voids for encapsulating the at least one therapeutic carrier.

11. The method of manufacturing the biodegradable porous sponge matrix of claim 1, wherein the first polymer is gelatin and the second polymer is polyvinyl alcohol.

12. The method of manufacturing the biodegradable porous sponge matrix of claim 11, wherein the concentration of gelatin is between 2%-7% w/v, and the concentration of polyvinyl alcohol is between 5%-15% w/v.

13. The method of manufacturing the biodegradable porous sponge matrix of claim 1 further comprising cutting the porous sponge matrix.

* * * * *